(12) United States Patent
Fischer et al.

(10) Patent No.: US 6,625,839 B2
(45) Date of Patent: Sep. 30, 2003

(54) FLOCKED TONGUE CLEANING DEVICE

(75) Inventors: Dan E. Fischer, Sandy, UT (US); Bruce S. McLean, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 209 days.

(21) Appl. No.: 09/801,974

(22) Filed: Mar. 8, 2001

(65) Prior Publication Data
US 2002/0019645 A1 Feb. 14, 2002

Related U.S. Application Data (63) Continuation-in-part of application No. 09/511,827, filed on Feb. 24, 2000, now abandoned, and a continuation-in-part of application No. 09/484,302, filed on Jan. 18, 2000, now abandoned.

(51) Int. Cl.[7] .............................. A46B 3/02; A61B 17/24
(52) U.S. Cl. ..................... 15/160; 15/111; 15/167.1; 15/176.4; 606/161
(58) Field of Search ................... 15/22.1, 111, 160, 15/167.1, 176.4; 132/308–310; 606/161

(56) References Cited

U.S. PATENT DOCUMENTS

| | | | |
|---|---|---|---|
| 2,218,072 A | 10/1940 | Runnels | 15/188 X |
| 3,943,592 A | 3/1976 | Bhaskar et al. | 15/160 |
| D243,422 S | 2/1977 | Varga | D4/104 |
| 4,079,478 A | 3/1978 | Andrews, Sr. | 15/210.1 |
| 4,404,977 A * | 9/1983 | Vasas | 15/207.2 X |
| D309,528 S | 7/1990 | Valenti | D4/104 |
| 4,958,402 A | 9/1990 | Weihranch | 15/207.2 |
| D332,352 S | 1/1993 | Caldwell et al. | D4/104 |
| 5,226,197 A | 7/1993 | Nack et al. | 15/111 |
| 5,337,436 A | 8/1994 | Saxer et al. | 15/104.94 |
| 5,438,726 A | 8/1995 | Leite | 15/105 |
| 5,613,262 A | 3/1997 | Choy-Maldonado | 15/160 |
| D388,616 S | 1/1998 | Wieder et al. | D4/111 |
| 5,735,864 A | 4/1998 | Heisinger, Jr. | 606/161 |
| 5,749,116 A | 5/1998 | Wieder et al. | 15/160 |
| 5,800,367 A | 9/1998 | Saxer et al. | 601/164 |
| D400,357 S | 11/1998 | Crosson | D4/111 |
| 5,842,247 A | 12/1998 | Decesare | 15/106 |
| D405,272 S | 2/1999 | Khalaj et al. | D4/110 |
| 5,866,116 A | 2/1999 | Yaegaki | 424/93.51 |
| 5,944,519 A | 8/1999 | Griffiths | 433/80 |
| 5,947,912 A | 9/1999 | Montagnino | 601/142 |
| 5,951,578 A | 9/1999 | Jensen | 606/161 |
| 6,049,934 A | 4/2000 | Disko | 15/106 |
| 6,131,228 A | 10/2000 | Chen et al. | 15/22.1 |
| 6,132,445 A | 10/2000 | Pavanelli | 606/161 |

FOREIGN PATENT DOCUMENTS

DE  2311043  9/1974

\* cited by examiner

*Primary Examiner*—Mark Spisich
(74) *Attorney, Agent, or Firm*—Workman, Nydegger (57) ABSTRACT

A brush for cleaning a user's tongue is disclosed. The tongue cleaning device includes an elongated handle that is sized and configured to be comfortably grasped by the user. A cleansing head is attached to the elongated handle having a brush portion. The brush portion has a plurality of flocked fibers. The brush portion may be permanently or removably attached to the cleansing head.

11 Claims, 7 Drawing Sheets

FLOCKED TONGUE CLEANING DEVICE

RELATED APPLICATIONS

This application is a continuation-in-part patent application of U.S. patent application Ser. No. 09/511,827 entitled Tongue Cleaning Device and Related Methods, which was filed on Feb. 24, 2000 now abandoned. Ser. No. 09/511,827 is a continuation-in-part patent application of U.S. patent application Ser. No. 09/484,302 entitled Tongue Brush which was filed on Jan. 18, 2000, now abandoned, on behalf of Dan E. Fischer and Bruce S. McLean. Ser. No. 09/511,827 and Ser. No. 09/484,302 are both incorporated herein by specific reference.

BACKGROUND OF THE INVENTION

1. The Field of the Invention

The present invention generally relates to an oral hygiene device and, in particular, to a tongue cleaning device that provides for convenient and effective cleaning of the tongue, without causing the user to gag or choke.

2. Description of Related Art

Proper care of a person's mouth or oral cavity is very important for good oral hygiene. Generally, individuals who desire good oral hygiene brush and floss their teeth on a consistent basis, but they frequently neglect to clean their tongue. The tongue is important to clean because bacteria, food and other foreign matter can buildup on the dorsum or upper surface of the tongue. In order to have good oral hygiene, these materials need to be carefully removed from the outer surface of the tongue.

The tongue, however, is not easy to clean because it is an irregularly shaped, mobile mass of striated muscles that can rapidly change its shape and configuration. Additionally, the tongue is difficult to clean because it has a rough, nonuniform outer surface and it is covered with mucous membrane. In greater detail, the tongue includes a front or anterior portion that constitutes about two-thirds of the body of the tongue. This front portion of the tongue, which includes the apex or tip, is generally positioned horizontally in the mouth and it is thickly covered with various types of papillae. The papillae project outwardly from the upper surface of the tongue to create the roughened surface. The rear or posterior portion of the tongue, located near the throat, typically has a more nodular or bossed surface and it is covered with numerous muciparous glands and lymph follicles. The tongue also includes about 5,000 to 10,000 taste buds that are scattered over the upper and side surfaces of the tongue. These different structures and surfaces create numerous mounds, ridges, peaks, protrusions, furrows, grooves and folds of various shapes and sizes. This lack of evenness makes cleaning the tongue very difficult because food particles and other debris often become trapped or encrusted in these various nonuniform surfaces.

It is known to use conventional toothbrushes to clean the tongue. The long bristles of conventional toothbrushes, however, are designed to clean the hard outer surfaces of the teeth and the long bristles are pliable to minimize abrasiveness to the enamel surfaces of the teeth. The long bristles of conventional toothbrushes are also designed to create toothpaste lather, contact the gums, reach below the gingival tissue and not damage the teeth or surrounding gingival tissue. Additionally, the long bristles allow the toothbrush to reach into the crevices between and around teeth, while providing a safe margin between the tips of the bristles and the hard plastic base of the toothbrush. Further, conventional toothbrushes often have an elongated head with a narrow width to fit into the constricted areas of the mouth, such as between the teeth and the cheek. Accordingly, conventional toothbrushes have a narrow width and a high profile measured from the tips of the bristles to the outer surface of the head of the toothbrush.

The long bristles of conventional toothbrushes, however, are not suitable to reach and clean the bottom surfaces of the various folds, grooves and ridges in the tongue because the bristles are not sufficiently rigid. Additionally, the long bristles and relatively thick body of the toothbrush often touch the pharynx, soft palate or posterior portion of the mouth and this frequently elicits a "gagging" or "choking" response by the user. Further, while the generally slender configuration of a conventional toothbrush allows it to fit into the narrow spaces between teeth and cheek, it prevents the toothbrush from quickly or efficiently cleaning the tongue because of its small contact area. Accordingly, conventional toothbrushes are generally unsuitable for cleaning the tongue.

In response to the need for brushes and other devices specifically designed for cleaning the tongue, various designs have been developed as disclosed in U.S. Pat. No. 5,951,578 issued to Jensen, U.S. Pat. No. 5,944,519 issued to Griffiths, U.S. Pat. No. 5,842,247 issued to Decesare, U.S. Pat. No. 5,735,864 issued to Heisinger, Jr., U.S. Pat. No. 5,749,116 issued to Wieder et al., U.S. Pat. No. 5,735,864 issued to Heisinger, Jr., U.S. Pat. No. 5,613,262 issued to Choy-Maldonado, U.S. Pat. No. 4,079,478 issued to Andrews, U.S. Pat. No. 3,943,592 issued to Bhaskar et al., U.S. Design Pat. No. 243,422 issued to Varga, U.S. Design Pat. No. 405,272 issued to Khalaj et al., U.S. Design Pat. No. 400,357 issued to Crosson, U.S. Design Pat. No. 388,616 issued to Wieder et al., U.S. Design Pat. No. 332,352 issued to Caldwell et al., U.S. Design Pat. No. 309,528 issued to Valenti, and U.S. Design Pat. No. 243,422 issued to Varga.

One design approach described in several of these patents is to use the same type of clusters of bristles used with conventional toothbrushes which have been shortened to minimize the occurrence of the gag reflex. Such fibers are typically made from nylon. Examples of such designs are disclosed in U.S. Pat. No. 5,842,247 issued to Decesare U.S. Pat. No. 5,749,116 issued to Wieder et al., U.S. Pat. No. 5,613,262 issued to Choy-Maldonado, U.S. Design Pat. No. 332,352 issued to Caldwell et al., U.S. Design Pat. No. 309,528 issued to Valenti, and U.S. Design Pat. No. 243,422 issued to Varga.

There are several problems with such brushes that utilize clusters of fibrous bristles. Since the bristles are typically made of nylon, the shortness of the bristles tends to result in insufficient flexibility. More particularly, the short bristles are too stiff and are resultingly incapable of adequately conforming to the varied surface features and contours of the tongue to optimally clean the tongue. Additionally, since the rigidity increases as the length is decreased, the length cannot be sufficiently reduced to result in a desirable vertical profile. The vertical profile includes the combined height of the bristles and the head from which the bristles extend.

As indicated above, it is desirable to reduce the vertical profile as much as possible in order to minimize the likelihood of inducing a gag reflex. The tongue brush sold by Enfresh Products LLC is an example of a tongue brush with a reduced vertical profile. These brushes have a head with clusters of fiber bristles extending from the head. Note that the brushes sold by Enfresh Products LLC are marked with Design Pat. No. 400,357 which issued to Crosson. In addition to Design Pat. No. 400,357, these tongue brushes can be viewed at www.enfresh.com. The tongue brushes marked with Design Pat. No. 400,357 have a vertical profile of about 0.4 inches or 10.16 mm. Note that the clusters of fibrous bristles of the tongue brushes, which are marked with Design Pat. No. 400,357, have a length of about 0.2 inches or 5.8 mm and are very stiff. The bristles in the brush sold by Enfresh Product LLC are relatively stiff as they are made from the same material as toothbrush bristles but are much shorter. More particularly, the bristles have a length to thickness ratio of about 40:1 while toothbrush bristles have a length to thickness ratio of about 75:1.

Another tongue brush having clusters of bristles has an even smaller vertical profile. U.S. Pat. No. 5,951,578 issued to Jensen indicates at column 4, lines 36–41 that the preferred vertical profile of the brush disclosed therein is approximately 5/16 inches (0.3125 inches and 7.9375 mm) based on the combined thickness of the forward end 36 of the brush and the associated bristles.

One approach to achieving a reduction in the vertical profile is disclosed in U.S. Pat. No. 3,943,592 issued to Bhaskar et al. Bhaskar et al. utilizes a laminate of Velcro® tape adhered onto an elongated member. As indicated at column 6, line 21 in Bhaskar et al., the resulting combined vertical profile of the tape on the elongated member is 3 mm. Bhaskar et al. indicates that this lower profile provides a significant advantage over the use of toothbrushes, which have a vertical profile of 15 mm. However, the structure used to achieve this low profile is not easily cleaned for repeated use. More particularly, the hooks of the Velcro® tape are not easily cleaned. Additionally, adhesion of the other adhesive side of the tape to wood may lead to bacterial growth that is difficult to eliminate. Accordingly, a tongue brush having a head with two parts including a laminate brush portion adhered onto a head such as that disclosed in U.S. Pat. No. 3,943,592 may not be useable in a repeated manner due to the difficulty involved in cleaning it. U.S. Pat. No. 4,079,478 issued to Andrews is another laminate that presents similar difficulties in maintaining the brush in a clean condition for repeated use. Obviously retention of residual bacteria diminishes the ability of such brushes to effectively clean.

A tongue brush having clusters of fibrous bristles, such as those discussed above, can also be difficult to maintain in a clean condition. More particularly, since the bristles are held very tightly together, particularly at the base of the cluster, the cluster may not be fully clean when used again. Further, since the bristles extend into the head some portions may even be impossible to fully clean.

Another approach to tongue cleaning is disclosed in U.S. Pat. No. 5,944,519 which issued to Griffiths. The cleaner has a compressible foam pad that has been folded onto a handle. The compressible pad is covered with fibers that have been flocked onto its surface so that the entire surface of the compressible pad can be used to clean the tongue. The compressible pad is a porous foam so that it can hold mouthwash. However, a disadvantage resulting from the porosity of the foam is that it may be difficult to adequately clean it. Another disadvantage is that the manner in which the pad is adhered to the handle causes it to have a large vertical profile.

Further, various mechanical devices to clean a person's tongue are also known. These devices are generally complex mechanical systems that agitate the bristles of the brush. These complex devices, however, are expensive, prone to breaking and difficult to control.

SUMMARY OF THE INVENTION

A need therefore exists for a tongue cleaning device that provides convenient and effective cleansing of the tongue, and eliminates the above-described disadvantages and problems.

One aspect of the present invention is a tongue cleaning device that can remove food, debris, bacteria, plaque and other matter from the plurality of grooves, furrow and folds in the outer surface of the tongue. The tongue cleaning device includes an elongated body with a handle and a cleansing head. The handle is ergonomically designed to allow the user to hold the tongue cleaning device comfortably and in proper alignment with the outer surface of the tongue.

The cleansing head includes a brush portion with a plurality of flocked fibers adhered onto the brush portion by an adhesive. The tongue cleaning device may also include a scraper to assist in scraping away food and other foreign matter from the tongue. It will be appreciated that while the tongue cleaning device can be used with a cleanser, use of the cleanser is not required.

The brush portion is preferably an integral portion of the head. The brush portion may also be molded into an aperture in the head as part of a two-part molding process such that the brush portion and the head are sealed together. The brush portion may also be separately formed as a brush insert that is inserted into an aperture in the head.

As indicated above, the fibers of the cleansing head, more particularly the brush portion, are flocked onto the brush portion. The fibers allow the tongue cleaning device to cleanse the tongue by dislodging bacteria, food and other matter from the outer surface of the tongue. Advantageously, the fibers allow intense scrubbing of the deeper furrows, folds and grooves on the upper surface of the tongue. Additionally, the tongue cleaning device can clean both the macroscopic and microscopic portions of the tongue effectively.

A significant advantage of the use of flocked fibers is the resulting vertical profile of the cleansing head and fibers, thereby minimizing the potential for eliciting a gag reflex when cleaning the tongue. In particular, the cleansing head has a relatively small thickness and the fibers have a relatively short length such that the overall profile of the cleansing head is relatively thin. This allows the cleansing head to clean the posterior portion of the tongue without touching the pharynx, soft palate or posterior portion of the mouth and causing a gag reflex.

The present invention is advantageously simple to manufacture and it requires little or no assembly. Thus, the manufacturing costs are relatively inexpensive. Additionally, the tongue cleaning device can be readily cleaned and reused, or it can be readily disposed. The tongue cleaning device may also include a replaceable brush portion that allows the brush portion to be replaced, or a brush portion with a different type or fibers to be used.

Further aspects, features and advantages of the present invention will become apparent from the detailed description of the preferred embodiments that follows.

BRIEF DESCRIPTION OF THE DRAWINGS

The appended drawings contain figures of preferred embodiments of the present tongue cleaning device. The above-mentioned features of the tongue cleaning device, as well as other features, will be described in connection with the preferred embodiments. The illustrated embodiments, however, are only intended to illustrate the invention and not limit the invention. The drawings contain the following figures.

DETAILED DESCRIPTION OF THE PREFERRED EMBODIMENTS

The present invention is generally directed towards a tongue cleaning device that provides convenient and effective cleansing of the tongue. The principles of the present invention, however, are not limited to tongue cleaning devices. It will be understood that, in light of the present disclosure, the tongue cleaning device disclosed herein can be successfully used in connection with other types of oral hygiene devices.

Additionally, to assist in the description of the tongue cleaning device, words such as top, bottom, front, rear, right and left are used to describe the accompanying figures. It will be appreciated, however, that the present invention can be used in a variety of desired positions—including various angles, sideways and even upside down.

A detailed description of the tongue cleaning device now follows. Note that, the main components of the tongue cleaning device including the handle 12 and the head 22 are described and then the unique features of the brush portion 44 and its flocked fibers 46 are described in detail.

Figure 1A:
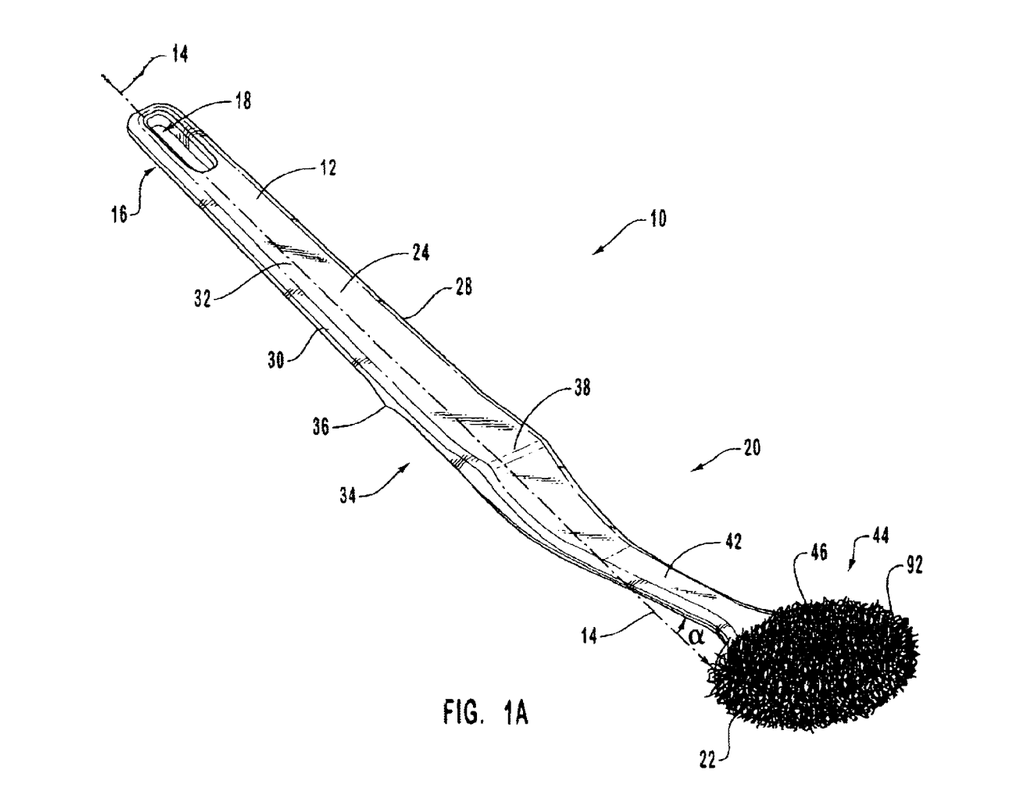
FIG. 1A is a perspective view of a tongue cleaning device in accordance with a preferred embodiment of the present invention.
Figure 1B:
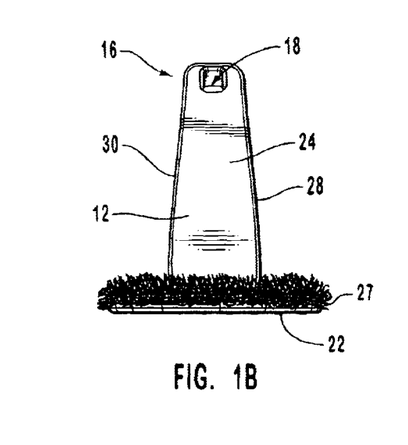
FIG. 1B is a front view of the tongue cleaning device shown in FIG. 1A.

As seen in FIG. 1A, the tongue cleaning device 10 includes an elongated handle 12 that extends generally along a longitudinal axis 14. The handle 12 includes a first end 16 with an aperture 18 that allows the tongue cleaning device 10 to be hung or supported, and a second end 20 with a cleansing head 22. The cleansing head 22 is integrally attached to the handle 12 to form a one-piece tongue cleaning device 10, but the head can also be removably or permanently attached to the handle. The handle 12 has a generally rectangular cross-section with an upper surface 24, a lower surface 26, a right side 28 and a left side 30. The ends, surfaces and sides of the tongue cleaning device 10 are rounded or curved for comfort and safety.

The elongated handle 12 is constructed of a generally rigid material such as plastic. In particular, the handle 12 may be constructed from various materials including synthetic materials and polymers such as polyethylene, polypropylene, vinyl or nylon. The handle 12 has a length between about 5 inches to about 7 inches measured from the first end 16 to the second end 20, a width of about 0.5 inches and a thickness of about 0.125 inches, but the handle can have any suitable size or dimensions depending upon, for example, the type of materials used to construct the handle or the intended use of the tongue cleaning device 10. For instance, the handle 12 could be larger if the tongue cleaning device 10 is intended to be used by adults, or smaller if it is intended to be used by children.

Advantageously, the handle 12 is ergonomically designed to allow the user to comfortably hold the tongue cleaning device 10. Specifically, the handle 12 includes a generally straight body portion 32 in which the upper surface 24 is generally parallel to the lower surface 26. The handle 12 also includes gripping portions 34 with one or more curved surfaces to allow the user to easily hold the tongue cleaning device 10. The gripping portions 34 include a first arcuate portion 36 located on the lower surface 26 and a second arcuate portion 38 located on the upper surface 24 of the handle 12. These arcuate portions 36 and 38 are designed to provide an engagement fit with the fingers and thumb of the user, respectively, and prevent the handle 12 from slipping during use of the tongue cleaning device 10. Additionally, the handle 12 may include gripping portions that are textured, have nonslip surfaces or include various types of outwardly extending projections that allow the user to securely grip the tongue cleaning device 10. These various gripping portions may be especially beneficial if the handle is wet or being cleaned.

The handle 12 and the gripping portions 34 aid in properly positioning the tongue cleaning device 10 relative to the tongue. Specifically, the handle 12 and gripping portions 34 help position cleansing head 22 generally parallel to the outer surface of the tongue. In contrast, the handle of a conventional toothbrush is often designed to position the toothbrush head at an angle relative to the user's teeth. Additionally, the handle 12 and gripping portions 34 of the tongue cleaning device 10 are equally effective for right and left handed users.

Figure 1C:
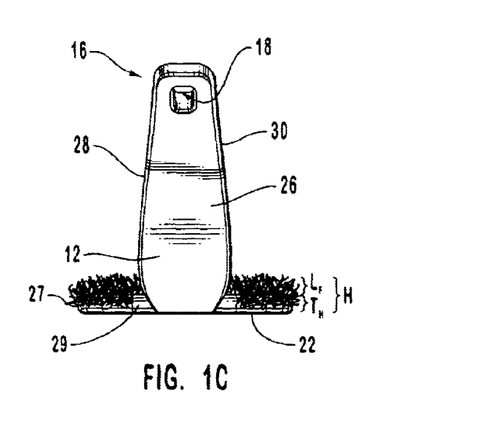
FIG. 1C is a back view of the tongue cleaning device shown in FIG. 1A.
Figure 1D:
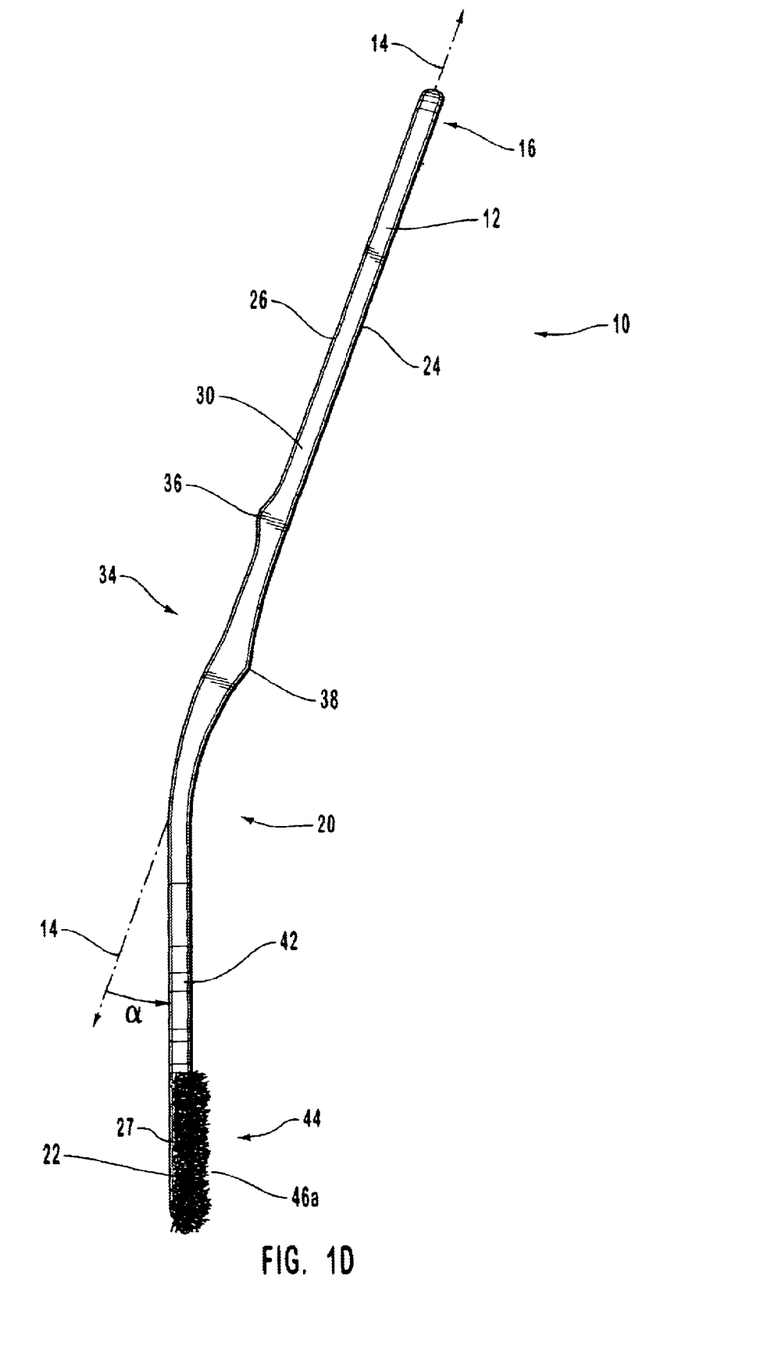
FIG. 1D is a right side view of the tongue cleaning device shown in FIG. 1A, with the left side being a mirror image thereof.
Figures 1E, 1F:
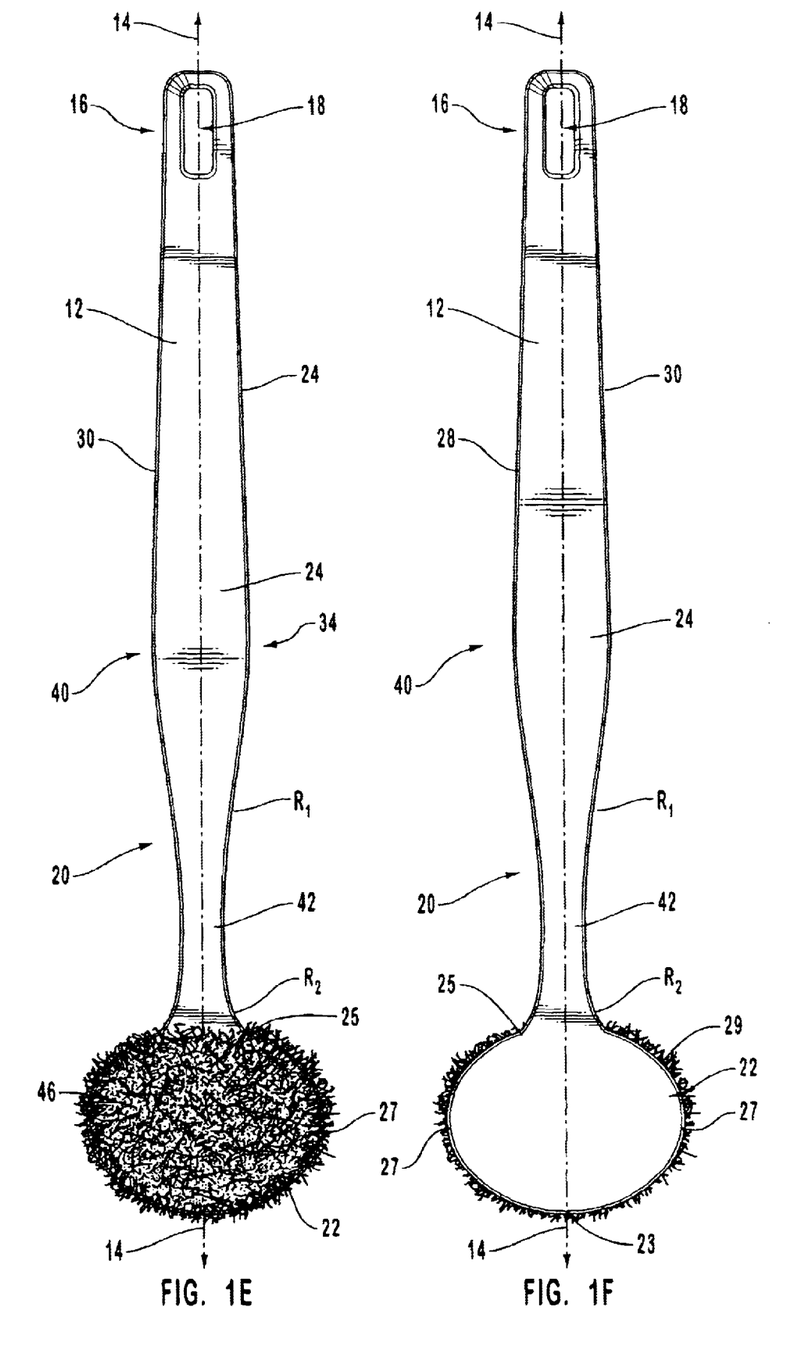
FIG. 1E is a top view of the tongue cleaning device shown in FIG. 1A.
FIG. 1F is a bottom view of the tongue cleaning device shown in FIG. 1A.
Figure 1G:
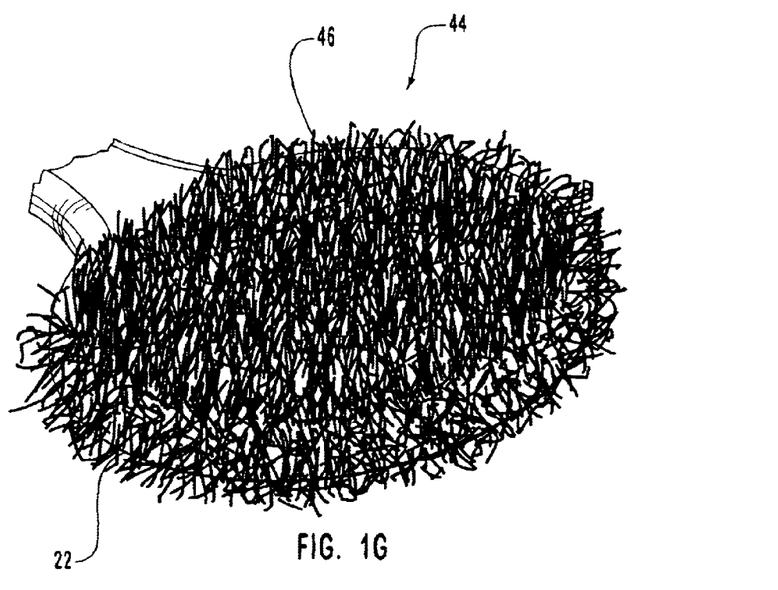
FIG. 1G is an enlarged partial perspective view of the tongue cleaning device shown in FIG. 1A, illustrating the brush portion.
Figure 1H:
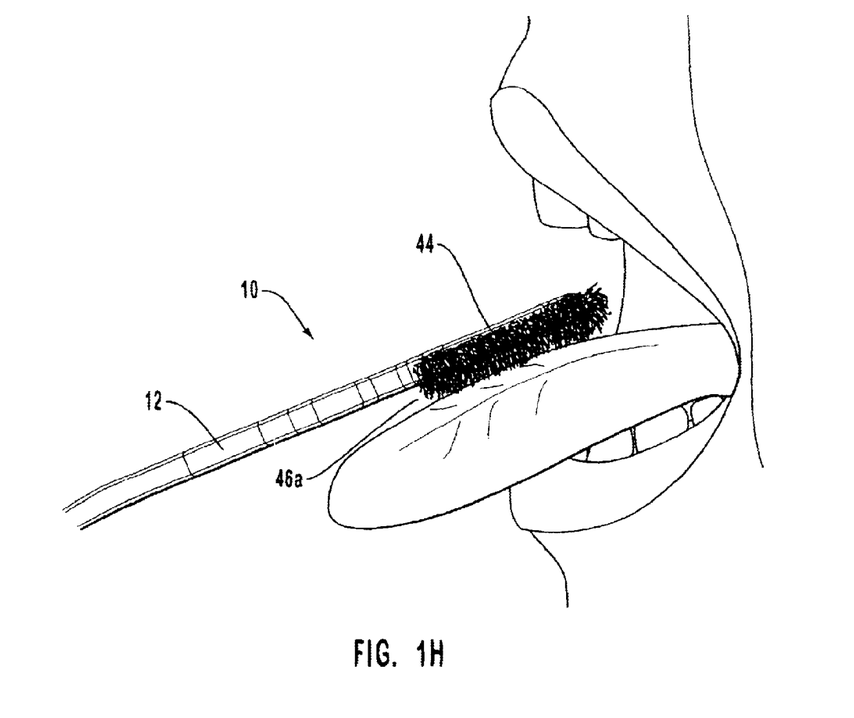
FIG. 1H is an enlarged partial perspective view of the tongue cleaning device shown in FIG. 1A, illustrating the brush portion being pulled across a tongue.

As best seen in FIG. 1E and FIG. 1F, the right side 28 and the left side 30 of the handle 12 are tapered. Preferably, the sides 28 and 30 are tapered in a generally linear manner from a central portion 40, located proximate the gripping portions 34, towards the first end 16 of the handle 12. Preferably, the central portion 40 has a width of about 0.6 inches and the first end has a width of about 0.4 inches. The sides 28 and 30 are also tapered from the central portion 40 towards a neck 42 located between the cleansing head 22 and the handle 12. The narrowed neck 42 allows the cleansing head 22 to be easily inserted and moved within the user's mouth. The neck 42 is preferably smoothly tapered at a first radius of curvature $R_1$ from the central portion 40 to the neck 42 and at a second radius of curvature $R_2$ from the neck 42 to the cleaning head 22. It will be appreciated, however, that the cleansing head 22 can be connected to the handle 12 in any desired manner and the handle 12 can have any suitable shape and configuration. The transition from neck 42 to cleansing head 22 is considered to be an end of handle 12.

The general shape and configuration of handle 12 enables tongue cleaning device 10 to be stored in a similar manner and location as a conventional toothbrush. Additionally, the tongue cleaning device 10 can be hygienically cleaned by rinsing it. It will be appreciated, however, that the tongue cleaning device 10 can be cleaned and stored in any suitable manner. Alternatively, the tongue cleaning device 10 can be disposed of after use. Handle 12 is an example of handle means for enabling a user to grasp one end of the tongue cleaning device as the opposite end is directed by the user to facilitate a cleaning procedure in the user's mouth.

As best seen in FIG. 1E and FIG. 1F, cleansing head 22 has a curved shape with elongated opposing lateral ends 27. More particularly, cleansing head 22 is oblong or elliptical as its lateral ends 27 extend outward such that the distance between its lateral ends 27 is greater than the distance from its top 23 to its base 25 which transitions to neck 42. Other cleansing heads are shown that are generally circular at 22' and 22" respectively in FIG. 2A and FIG. 3A. It will be appreciated, however, that the cleansing head 22 can have any suitable size or shape such as oval, elongated, circular or rectangular. If the cleansing head is noncircular, it preferably has smooth, rounded corners to prevent abrasion and irritation of the mouth.

The preferred outside diameter of a cleansing head having a circular configuration is about 1.125 inches so that the head fits comfortably within the user's mouth and to maximize the cleaning area. While the cleansing head 22 may have an outside diameter that is larger than about 1.125 inches for adults, the diameter may be about 1.0 inches or smaller for children. As best seen in FIG. 1A and FIG. 1D, neck 42 is at an angle relative to straight body portion 32. Since cleansing head 22 extends from neck 42, the angle of neck 42 relative to straight body portion 32 determines the angle between cleansing head 22 and handle 12. The angle, identified in the FIG. 1A and FIG. 1D as α, between cleansing head 22 and handle 12 is of about 20°. An angle α of about 20° facilitates cleaning of the tongue, but the angle can be larger or smaller, depending, for example, upon the configuration of the handle 12 or intended use of the tongue cleaning device 10. Such an angle enhances the ability to pull fibers 46 across the tongue while also pushing downward. More particularly, the angle provides increased leverage so that it is easier to apply pressure to the tongue.

Another advantage of the angled configuration is that the neck 42 and cleansing head 22 may be inserted far into mouth since the angle configuration resembles the shape of the tongue. Note that due to this angled configuration, only one side of cleansing head 22 is typically flocked and utilized in a tongue cleaning procedure. More particularly, when the handle is angled as shown then it is only usefully used with one orientation for cleaning the far reaches of the tongue as the tongue extends downward in the user's throat. An advantage of having flocked fibers on only one side of cleansing head 22 is that the vertical profile is minimized.

As best shown in FIG. 1E and FIG. 1F, cleansing head 22 has a bare back side and a bare transition to neck 42 beginning at base 25. As discussed above, it is preferred to have a bare back surface in order to minimize the vertical profile. However, in some embodiments both the front surface and the back surface of the cleansing head may be covered. Note that in contrast to head 22', the entire perimeter of cleansing head 22 is covered with flocked fibers such that some fibers extend from the sides 29 of cleansing head 22. This configuration maximizes the ability of cleansing head to clean the tongue.

The brush portion in all of these embodiments is essentially the portion of the tongue cleaning device onto which the fibers are flocked. For example, in the embodiment shown in FIGS. 1A–1H, brush portion 44 is the part of cleansing head 22 that has been flocked. As described in detail below, the cleansing head may have a brush portion that is an integral portion of the cleansing head on which the fibers have been flocked while portions of the cleansing head such as the perimeter are bare as discussed below in reference to head 22'. Alternatively, the brush portion can also be integrally molded into an aperture in the cleansing head as also discussed below in reference to head 22'. Additionally, the brush portion may be separately formed for subsequent insertion into the cleansing head as discussed below in reference to head 22". The brush portions described herein are all examples of brush means for cleaning tongue surfaces via flocked fibers attached to the brush means as the brush means is moved by a handle.

The fibers 46 used to cover or flock cleansing head 22, or more particularly brush portion 44, may have any suitable length and diameter or fineness. A preferred length is in a range from about 0.125 inches (about 3 mm) to about 0.15 inches (about 4 mm). The range is more preferably from about 0.04 inches to about 0.12 inches and is most preferably from about 0.06 inches to about 0.1 inches. The fibers 46 can also have a variety of different lengths. In one embodiment, short and long fibers are flocked onto the cleansing head such that the long fibers are supported by the short fibers. The combination of lengths may assist in cleaning the irregular surfaces of the tongue. The fibers may also have either the same diameter or a plurality of diameters. The range of diameters that is preferred is from about 25 denier to about 100 denier. The diameter range is preferably from about 45 denier to about 100 denier and is most preferably from about 65 denier to about 100 denier.

When fibers are desired that are considered relatively short and small, fibers may be used that have a length of about 0.065 inches and a diameter of about 45 denier. In contrast, when fibers are desired that are considered to be relatively large and long, the fibers may have a length of about 0.08 inches and a diameter of about 100 denier. The combined use of fibers that are small and short fibers with fibers that are large and long is an example of a useful combination of different types of fibers. Preferred fibers have a length of about 0.065 inches and a diameter of about 100 denier.

Both synthetic and natural fibers may be used. Suitable synthetic fibers include nylon and polyester fibers while suitable natural fibers include cotton fibers. The fibers may optionally be formed from polypropylene, polyethylene or another thermoplastic elastomer material having a hardness comparable to polypropylene or polyethylene.

Fibers 46 can be affixed to cleansing head 22, or more particularly brush portion 44, in a variety of different well known methods such as through electrostatic flocking. According to one flocking method, an adhesive is applied to cleansing head 22 where fiber attachment is desired. The adhesive used to attach the fibers to cleansing head 22 is preferably water insoluble, for example, the adhesive may be polyurethane. A polyurethane adhesive has a desired degree of flexibility and water insolubility. An acrylic adhesive may be used that is flexible. Such adhesives are preferably light cured. Other adhesives that may be useful include epoxies and silicones, although, these are generally less flexible. Another flock adhesive is disclosed in U.S. Pat. No. 5,185,402 which is hereby incorporated by reference. An appropriate quantity of fibers is then contacted with the adhesive material. The adhesive is allowed to harden, thereby securing the fibers to the desired portion. Further information regarding methods for adhering fibers to a cleansing head can be obtained from U.S. patent application Ser. No. 09/702,284 entitled Cushioned, Fiber-Covered Dental Applicators filed on Oct. 30, 2000 and U.S. patent application Ser. No. 09/496,275 entitled Electrostatically Flocked Fishing Lures and Related Systems and Methods, both of which are hereby incorporated by reference. An additional method of fiber attachment is to injection or insertion mold the fibers onto the desired cleansing head. Thus, in one embodiment, the fibers are in a diameter and length which allows injection or insertion molding.

Fibers 46 may extend from cleansing head 22 primarily in a perpendicular configuration as shown. However, the fibers may also extend with other orientations such as a slanted configuration, crisscross configuration or in a random configuration.

Fibers 46 may have any suitable density. However, the fibers are preferably dense enough such that the tongue is touched by the fibers and not by the cleansing head 22 with the exception of its uncovered perimeter.

Cleansing head 22, or more particularly brush portion 44, has a thickness denoted in FIG. 1C as $T_H$. The thickness of cleansing head 22 is relatively small to minimize its contribution to the vertical profile or overall height denoted as H in FIG. 1C which is the combination of the thickness of cleansing head 22 and the length that fibers 46 extend beyond cleansing head 22 identified in FIG. 1C as $L_F$. The cleansing head 22 is also preferably sufficiently thick and rigid to enable a user to apply pressure to the tongue by pushing on handle 12 to adequately clean the tongue. The thickness of cleansing head 22 is preferably in a range from about 0.04 inches to about 0.125 inches, more preferably about 0.05 inches to about 0.08 inches, and is most preferably about 0.08 inches. The length that the plurality of flocked fibers 46 extend from said brush portion 44, as denoted in FIG. 1C as $L_F$, is not the length of the individual fibers but the length of fibers 46 as they are situated on brush portion 44. The length denoted in FIG. 1C as $L_F$ may range from about 0.1 inches to about 0.15 inches. The length is preferably no greater than about 0.13 inches, more preferably no greater than about 0.12 inches and most preferably about 0.1 inches.

The length of the fibers 46 is preferably minimized such that when combined with the thickness of cleansing head 22, $T_H$, the resulting vertical profile or height identified in FIG. 1C as H, is relatively small. By minimizing the vertical profile or height, the cleansing head can be inserted as far as possible while maximizing the clearance between the cleansing head and the top surface of the mouth. The reduced vertical profile also minimizes the risk of touching the pharynx, soft palate or posterior portion of the mouth in order to avoid causing a gag reflex. It has been found that the vertical profile or height is desirably minimized when it is no greater than about 0.3 inches (less than about 8 mm). However, it is still advantageous for the vertical profile to be even smaller. Accordingly, the combined height, H, resulting from the thickness of cleansing head 22, $T_H$, and the length of fibers 46, $L_F$, is preferably less than about 0.25 inches (less than about 6 mm), is more preferably less than about 0.2 inches (less than about 5 mm) and is most preferably less than about 0.18 inches. This reduced vertical profile provides a significant advantage over the prior art.

Cleansing head 22 and brush portion 44 are preferably not porous and not compressible. More particularly, cleansing head 22 and brush portion are preferably not resilient like a foam pad. The relatively stiff and nonporous nature of cleansing head 22 and brush portion 44 enables fibers 46 to be urged against the tongue without causing the cleansing head 22 or brush portion 44 to be compressed. The advantage is that the tongue can be cleaned with greater force and yet less effort is required to urge the fibers against one's tongue. Additionally, the nonporous nature of cleansing head 22 and brush portion 44 prevents the retention of moisture that may compromise the hygienic usefulness of the cleaning device.

The embodiment of tongue cleaning device 10 shown in FIGS. 1A–1H, depicts brush portion 44 as being integral with cleansing head 22. In this embodiment, brush portion 44 is the portion of cleansing head 22 from which flocked fibers 46 extend. More particularly, brush portion 44 is all of cleansing head 22 except for it back surface. The brush portion may comprise a smaller section of the cleansing head. For example, the section of the cleansing head comprising the brush portion may appear like brush portion 44' such that there is a bare perimeter around the brush portion. For a cleansing head that is integrally formed from a single material, the configuration of the brush portion depends on the placement of the adhesive used to hold the fibers onto the cleansing head.

Figures 2A, 2B, 2C:
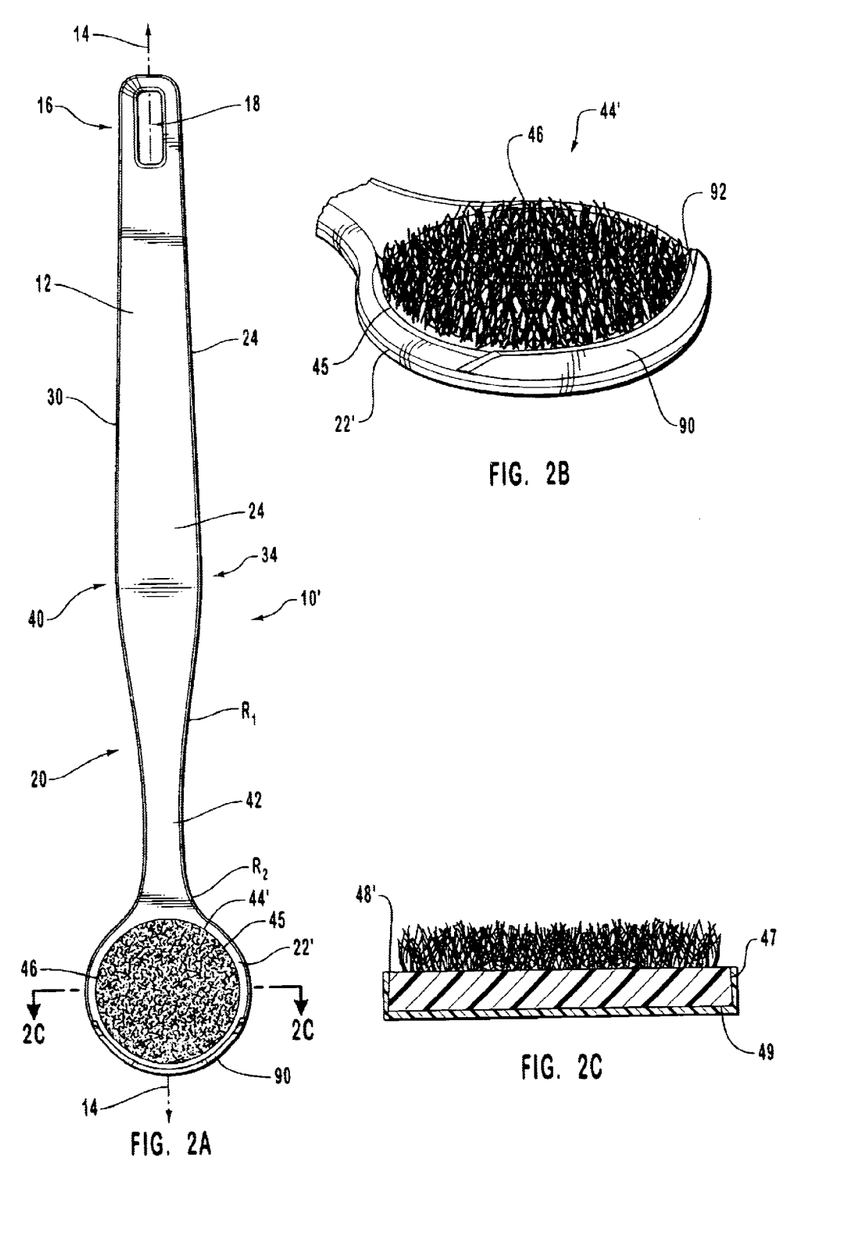
FIG. 2A is a top view of another embodiment of the tongue cleaning device having a brush portion molded into the head.
FIG. 2B is an enlarged partial perspective view of the tongue cleaning device shown in FIG. 2A, illustrating the cleansing head.
FIG. 2C is a cross-sectional view of the tongue cleaning device shown in FIG. 2A.

The embodiment described in reference to FIGS. 2A–2C has a brush portion 44' which is molded into cleansing head 22' so that brush portion 44' is sealed against cleansing head 22'. Accordingly, the perimeter of its top is not covered with fibers. Another embodiment is described in reference to FIGS. 3A–3D wherein the brush portion 44" is separately formed as a brush insert that is inserted into an aperture in the cleansing head 22". Note that additional fibers can also be adhered onto the remainder or to sections of cleansing head 22' or 22" to provide an appearance like that of cleansing head 22. Note also that these cleansing heads can also be shaped like cleansing head 22. These other embodiments are discussed in detail below.

Any suitable plastic material may be used to form the handle, cleansing head and brush portion. However, the plastic material used may depend on whether the cleansing head and the brush portion are integral or separate components. For example, nylon is a preferred material for an integral head and brush portion. When the brush portion is separate, it may be preferable to use low density polyethylene, polypropylene, copolymers of both polyethylene and polypropylene, or ethyl vinyl acetate.

As indicated above, the brush portion and cleansing head may also be molded together from different materials by conventional molding processes such as a two color molding process. In a two color molding process, one component is molded onto the other. For example, the brush portion may be molded into the aperture of the cleansing head after the cleansing head has been formed to yield a tongue cleaning device 10' as shown in FIGS. 2A–2C. This design is advantageous particularly when it is useful to have components of differing rigidity and flexibility. For example, it may be useful to form the handle from a material such as nylon so that it is relatively hard while the brush portion is formed from a softer plastic material such as low density polyethylene, polypropylene, copolymers of both polyethylene and polypropylene, or ethyl vinyl acetate. Note that while such softer plastic materials are not as rigid as nylon they are still preferably not resilient such as a foam pad and are not porous.

When viewing tongue cleaning device 10' as depicted in the drawings and comparing it with tongue cleaning device 10, the only apparent distinction is mold interface 45. While a mold interface is visible, the components are molded against each other so that there is a seal that prevents ingress. Although, molding the brush portion into the head enables two different materials to be used, it is easier to obtain an optimally minimized vertical profile when the entire tongue cleaning device is integrally molded.

Molding of brush portion 44' into cleansing head 22' can be achieved by any suitable method. For example, cleansing head 22' may have an aperture such as aperture 48" shown in FIG. 3A and be formed to have a configuration corresponding with that of cleansing head 22" described herein below. It is common to rely on holes or other structures to anchor one component to the other as one component is molded onto the other. Accordingly, the plastic material of the component being molded can flow into holes or other structures in a manner that securely locks both components together after the plastic has hardened. If the plastic material used to form the brush portion is deposited into the cleansing head then the cleansing head may have holes or other structures that can function as anchors to hold these components together. Such anchors are examples of interlocking portions. As indicated above, examples of such structures are described in reference to the configuration of cleansing head 22" and brush portion 44" in FIGS. 3A–3D.

It should be understood that the aperture in cleansing head 22' may be formed such as aperture 48" or in other suitable configurations. For example, the aperture may be configured as shown at 48' in FIG. 2C so that the aperture has a solid back as shown in FIG. 1F. Aperture 48' has a sidewall 47 extending up from a flat bottom surface 49. Sidewall 47 is slightly inclined to form an angle less than 90° so that sidewall 47 assists in maintaining brush portion 44' in aperture 48' and acts as an interlocking portion. Similarly, the sidewall may be configured with a lip to act as an interlocking portion. Note that flat bottom surface 49 may also have vent holes of varying configuration for assisting in the molding process.

Even simpler configurations can also be utilized. For example, sidewall 47 can also be formed without an angle as molding the brush portion 44' in the aperture tends to anchor the brush portion due to the seal formed between the material of the brush portion against that of the sidewall. Also, the brush portion can be formed in an aperture having a straight sidewall without a bottom surface.

Figures 3A, 3B, 3C:
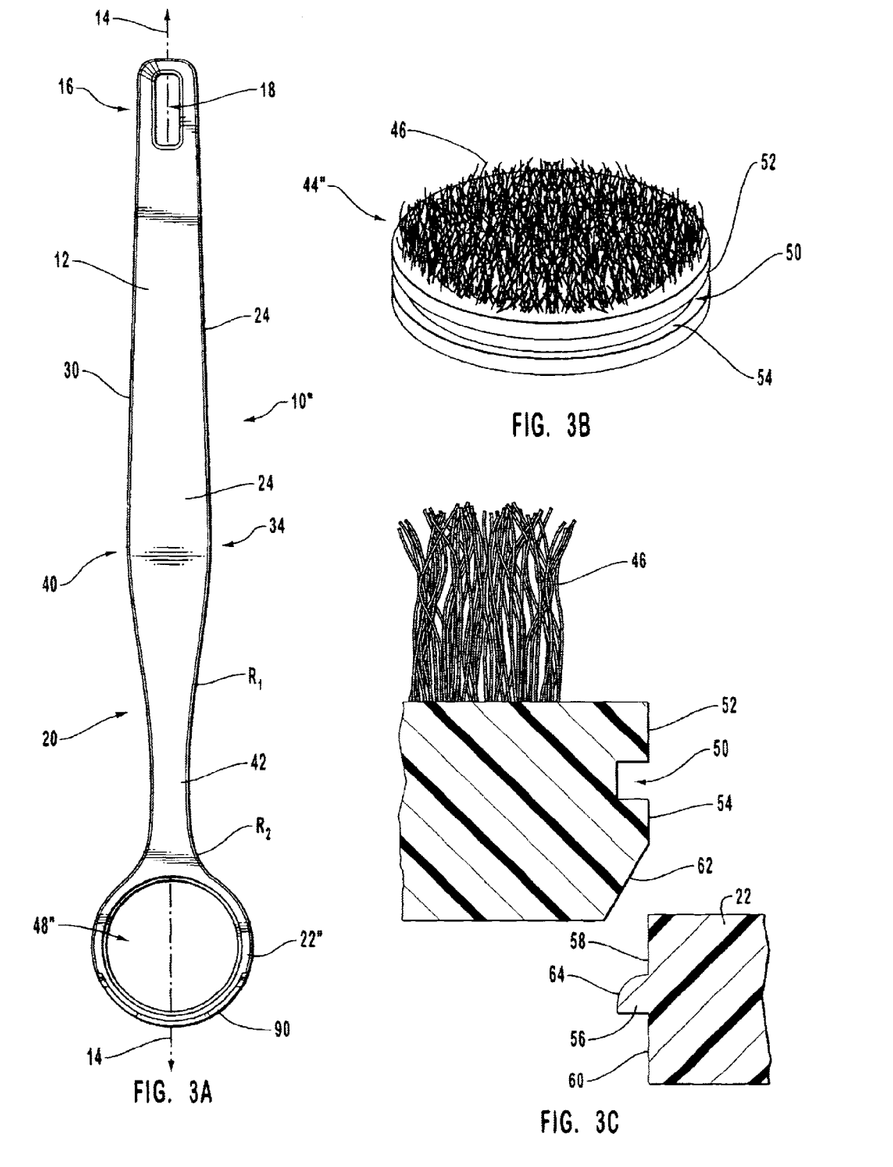
FIG. 3A is a top view of a tongue cleaning device in accordance with another preferred embodiment of the present invention, illustrating a brush portion removed from an aperture in the cleansing head.
FIG. 3B is an enlarged partial perspective view of the insertable brush portion configured for insertion into the aperture of the cleansing head shown in FIG. 3A.
FIG. 3C is an exploded cross-sectional side view of the tongue cleaning device shown in FIG. 3A, illustrating the brush portion and the cleansing head.
Figure 3D:
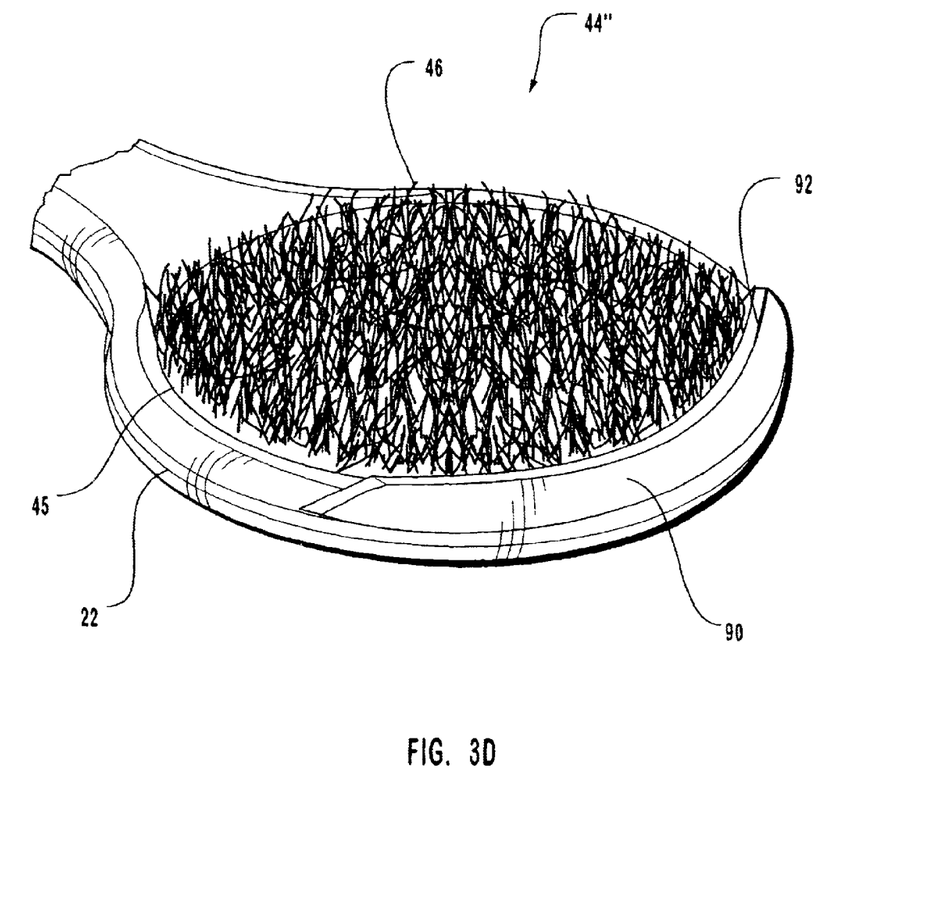
FIG. 3D is an enlarged partial perspective view of the cleansing head after insertion of the insertable brush portion shown in FIG. 3B.

As mentioned above, the cleansing head of the tongue cleaning device may be formed separately from the brush portion. As best seen in FIGS. 3A and 3D, such a cleansing head 22" of tongue cleaning device 10" includes an aperture 48" and a brush portion 44" sized and configured to be inserted and held within the aperture. The aperture 48" and the brush portion 44" preferably have a diameter of about 1.0 inch for a secure fit of the brush portion within the aperture, but the aperture and brush portion can be larger or smaller.

In greater detail, as best seen in FIGS. 3B and 3C, the brush portion 44" includes a groove 50 that is located between a first ridge 52 and a second ridge 54. The cleansing head 22" includes a radially inwardly extending flange 56 that is positioned between a first inner surface 58 and a second inner surface 60. The brush portion 44" is configured to be snap-fit into the aperture 48" to securely attach the brush portion to the cleansing head 22". Preferably, the second ridge 54 of the brush portion 44" includes an angled surface 62 and the inwardly extending flange 56 includes a curved upper surface 64 to facilitate the snap-fit connection. The snap-fit connection preferably requires a significant amount of force to insert the brush portion 44" into the aperture 48" to create a generally permanent connection. Alternatively, the snap-fit connection may be configured to allow the brush portion 44" to be removably attached to the cleansing head 22". Thus, for example, this allows the brush portion 44" to be replaced if worn or to use brush portions with different types or fiber configurations. It will be appreciated that the brush portion 44" can be attached to the cleansing head 22" by any suitable means, including an interference fit, sonic welding, adhesives, bonding, and the like.

Groove 50 of brush portion 44" is an example of an interlocking portion of brush portion 44". Flange 56 of cleansing head 22" is an example of an interlocking portion of cleansing head 22". Groove 50 and flange 56 are also examples of means for interlocking the brush portion and the cleansing head together in a manner such that the brush portion is received within the aperture of the cleansing head while preventing the subsequent removal of the brush portion. The advantage of this configuration is that brush portion 44 is so tightly held by cleansing head 22 that ingress is minimized of water, saliva, etc. which can lead to bacterial growth within the tongue cleaning device. Note that when the mated configuration of groove 50 and flange 56 is utilized, the interlocking portion of the cleansing head extends into the interlocking portion of the brush portion. In other embodiments, this configuration can be reversed such that the interlocking portion of the brush portion extends into the interlocking portion of the cleansing head. The interlocking portions described above in reference to FIGS. 2A–2C are also examples of interlocking means.

As shown in FIGS. 2A–2B, an optional scraper 90 is attached at the end of the cleansing head 22' of the tongue cleaning device 10'. The scraper 90 is used to scrape and remove foreign material and debris from the outer surface of the tongue. The scraper 90 may also be used to scrape and remove debris loosed by the brush portion 44. As best seen in FIG. 2B, the scraper 90 has a rounded upper surface 92 and it has a height of about 0.070 inches, which allows the scraper to clean the posterior portion of the tongue without touching the pharynx or soft palate. Thus, the scraper 90 minimizes the possibility of triggering the gag reflex. The scraper 90 is aligned with the outer surface of the cleaning head 22' to prevent debris and other material from accumulating between the end of the cleansing head 22' and the scraper. The scraper 90 is also positioned proximate the brush portion 44' to prevent debris and other material from accumulating between the fibers 46 and the scraper 90. The scraper 90 preferably extends about 120° about the circumference of the cleaning head 22', but the scraper could be larger or smaller. It will be understood that the scraper 90 could have any suitable dimensions and the tongue cleaning device does not require the scraper.

In sum, the tongue cleaning device 10 quickly and efficiently cleans the tongue without eliciting the gag reflex. Additionally, the fibers 46 remove food and other debris from the various ridges, grooves, furrows and other surfaces of the tongue without damaging or irritating the tongue. Further, the scraper 90 can also be used to remove foreign matter from the outer surface of the tongue. As described below, the tongue cleaning device 10 is easy to use and operate.

In operation, the user grasps the tongue cleaning device 10 by the handle 12 with either hand. The cleansing head 22 of the tongue cleaning device 10 is inserted into the mouth of the user with the fibers 46 facing downward, towards the dorsal surface of the tongue. The fibers 46 are placed in contact with the tongue and the tongue cleaning device 10 is moved relative to the tongue with the fibers engaging the dorsal surface of the tongue. The fibers 46 advantageously loosen and clean debris, plaque, food, etc. from the various grooves, furrows, papillae and the like from the outer surface of the tongue. That is, the fibers 46 independently contact and scrub the outer surface of the tongue. The scraper 90 can then be used to move the loosened debris and particles. Alternatively, the scraper 90 can be used to contact the tongue to assist in loosing the debris and other particles on the tongue. The user can then remove the debris from his or her mouth, for example, by rinsing, expectorating or swallowing.

Significantly, the cleaning process allows the dorsal surface of the tongue to be quickly and efficiently cleaned. Additionally, a gag reflex is not triggered because of the relatively small profile of the tongue cleaning device. Further, the large contact area of the tongue cleaning device 10 speeds the cleaning process and the fibers 46 independently contact and clean the varied outer surfaces of the tongue.

Although this invention has been described in terms of a certain preferred embodiment, other embodiments apparent to those of ordinary skill in the art are also within the scope of this invention. Accordingly, the scope of the invention is intended to be defined only by the claims that follow.

What is claimed is:

1. A tongue cleaning device comprising:
   an elongated handle having a first end and a second end,
   a cleansing head attached to said first end of the elongated handle,
   said cleansing head comprising an essentially flat brush portion having a plurality of flocked fibers of varying lengths adhered onto said brush portion by a flock adhesive,
   said flocked fibers being randomly adhered onto the brush portion so as to form a relatively stiff, nonporous brushing pad wherein the overall vertical profile of the cleansing head remains essentially flat and is minimized so that the cleansing head does not exceed about 0.3 inches (about 8 mm) in its overall dimension in order to help minimize the elicitation of a gag reflex when the device is used to clean the tongue.

2. The device as defined in claim 1, wherein said cleansing head has elongated opposing lateral ends.

3. The device as defined in claim 1, wherein said cleansing head is generally circular.

4. The device as defined in claim 1, wherein said brush portion and said cleansing head are molded together from different materials.

5. The device as defined in claim 1, further comprising an aperture in said cleansing head, wherein said brush portion is molded in said aperture.

6. The device as defined in claim 1, wherein said brush portion is adapted such that it remains substantially uncompressed as the handle is pushed downward toward the tongue to urge the plurality of flocked fibers against the tongue.

7. The device as defined in claim 1, wherein the plurality of fibers have a length in a range from about 0.0125 inches to about 0.15 inches.

8. The device as defined in claim 1, wherein the plurality of fibers have a diameter in a range from about 25 denier to about 100 denier.

9. The device as defined in claim 1, wherein the handle has a straight body portion and a neck, and wherein the cleansing head integrally extends from the neck, wherein there is an angle between the straight body portion and the neck to enable the cleansing head to extend far enough to reach one's throat and follow the curvature of the tongue as it extends down into the throat.

10. The device as defined in claim 1, wherein the handle has a straight body portion and a neck, and wherein the cleansing head integrally extends from the neck, wherein the cleansing head has a front and a back, wherein there is an angle between the straight body portion and the neck such that the handle has an angled configuration, and wherein the plurality of flocked fibers are adhered onto said brush portion primarily on the front of the cleansing head due to the angled configuration of the handle.

11. A tongue cleansing device comprising:
    an elongated handle, comprising a first end and a second end,
    a cleansing head connected to said first end of said elongated handle,
    an essentially flat brush portion having a plurality of flocked fibers adhered onto said brush portion,
    said flocked fibers being randomly adhered onto the brush portion so as to form a relatively stiff, nonporous brushing pad wherein the overall vertical profile of the cleansing head remains essentially flat and is minimized in order to help minimize the elicitation of a gag reflex when the device is used to clean the tongue, and
    wherein said brush portion and said cleansing head are configured in a manner so that they together provide a means for a removable snap-fit attachment of the brush portion to the cleansing head, thus permitting selective removal or replacement of the brush portion separate from the handle and its connected cleansing head.

* * * * *

UNITED STATES PATENT AND TRADEMARK OFFICE
CERTIFICATE OF CORRECTION

PATENT NO. : 6,625,839 B2
DATED : September 30, 2003
INVENTOR(S) : Dan E. Fischer and Bruce S. McLean It is certified that error appears in the above-identified patent and that said Letters Patent is hereby corrected as shown below:

Column 9,
Line 16, after "is to" please delete "injection" and insert -- inject --
Line 17, before "mold the" please delete "insertion" and insert -- insert --

Column 10,
Line 22, after "except for" please delete "it" and insert -- its --

Column 12,
Line 13, after "types" please delete "or" and insert -- of --
Line 43, after "debris" please delete "loosed" and insert -- loosened --

Column 13,
Line 15, after "assist in" please delete "loosing" and insert -- loosening --

Signed and Sealed this

Thirteenth Day of July, 2004

JON W. DUDAS
*Acting Director of the United States Patent and Trademark Office*